United States Patent [19]
Labonte, Jr.

[11] Patent Number: 5,989,497
[45] Date of Patent: Nov. 23, 1999

[54] PROCESS AND APPARATUS FOR DEODORIZING MALODOROUS SUBSTANCES WITH A CHLORINE DIOXIDE-CONTAINING COMPOSITION

[76] Inventor: Roland R. Labonte, Jr., 31 Grove Ave., North Kingston, R.I. 02852

[21] Appl. No.: 08/904,292

[22] Filed: Jul. 31, 1997

[51] Int. Cl.$^6$ ........................................ A61L 9/14
[52] U.S. Cl. .................... 422/5; 422/4; 422/123; 422/306; 422/900; 210/104; 423/210; 423/477; 424/661; 424/665
[58] Field of Search .................... 422/4, 5, 120, 422/123, 306, 900; 210/104, 139; 423/210, 477; 424/661, 665

[56] References Cited

U.S. PATENT DOCUMENTS

| | | | |
|---|---|---|---|
| 3,337,455 | 8/1967 | Wilson et al. | 210/63 |
| 3,355,019 | 11/1967 | Mitchell | 210/104 |
| 3,641,821 | 2/1972 | Neuberger et al. | 73/421 |
| 3,696,029 | 10/1972 | Walker | 210/14 |
| 3,804,253 | 4/1974 | Wellman et al. | 210/85 |

(List continued on next page.)

FOREIGN PATENT DOCUMENTS 2 696 643  4/1994  France .

OTHER PUBLICATIONS

S.L. Sarkar et al., "Concrete Deterioration Depth Profile Determination in Lift Station", Proc. Int. Conf. Cem. Microsc. 1996, 18th, 255–271 (Eng.)—Chemical Abstracts 125:17340h.

Katz, et al., "Disinfection of effluent by combinations of equal doses of chlorine and chlorine dioxide added simultaneously over varying contact times", Water Res. 28, 10 pp. 2133–2138 (1994)—Pollution Abs. 214474 95–03471.

Dernat, M. et al., "Water Management in Coastal Areas", Water. Sci. Technol. 25, 12, pp. 145–154 (1992)—Pollution Abs. 190916 93–03865.

Anonymous, "Treatment of industrial effluents", Effluent and Water Treatment Journal pp. 15–19 (Aug. 1979) Dialog–Pollution Abs. 069310 80–06264.

Yakovlev S.V., "The current state and perspective development and improvement of sewage in the USSR", Vodosnabzhenie I Sanitarnaia Tekhnika 3 pp. 5–7 (1979)—Pollution Abs. 066459 80–03409.

Rauh, J.S., "Disinfection and oxidation of wastes by chlorine dioxide", Journal of Environmental Sciences, 22, 2. pp. 42–45 (Mar.–Apr. 1979)—Pollution Abs. 064909 80–01856.

Kawata K., et al., "The search for effective wastewater disinfectants", Water Sewage Works, Ref. No. R–107–R–113 (1979)—Pollution Abs. 964881 80–01828.

(List continued on next page.)

*Primary Examiner*—Robert J. Warden, Sr.
*Assistant Examiner*—Fariborz Moazzam
*Attorney, Agent, or Firm*—Margaret B. Kelley, Esq.; Rogers & Wells LLP

[57] ABSTRACT

A process and apparatus are provided for deodorizing malodorous solids, liquids, and/or gases by contacting them with a mist of an aqueous deodorizing solution consisting of an alkali metal or alkaline earth metal chlorite, buffering agent(s), water, and optionally an alkali metal or alkaline earth metal chlorate and/or an alkali metal alkaline earth metal chloride. The preferred alkali metal is sodium. The deodorizing solution contains available chlorine dioxide and has a pH of about 8.5–9.5. In the process a concentrated solution of the deodorizing solution is diluted and mixed with water and misted into or onto the substance(s) to be deodorized, for example, the sewer gases from a sewage lift station. The apparatus consists of a rotameter which measures the amount of the concentrated deodorizing solution introduced into an eductor for dilution in a passing water stream which is then transported to spray nozzles for misting the malodorous substance(s). Preferably, a timer or monitor is incorporated so that the apparatus can be operated intermittently or continuously and the amounts of the oxidizing agents supplied can be varied.

23 Claims, 1 Drawing Sheet

U.S. PATENT DOCUMENTS

| | | | |
|---|---|---|---|
| 3,923,955 | 12/1975 | Fattinger | 423/210 |
| 3,975,284 | 8/1976 | Lambert | 252/187 |
| 4,250,144 | 2/1981 | Ratigan | 422/112 |
| 4,731,193 | 3/1988 | Mason et al. | 252/95 |
| 4,776,409 | 10/1988 | Manchak, Jr. | 175/50 |
| 4,823,826 | 4/1989 | Sacco | 137/1 |
| 4,844,874 | 7/1989 | deVries | 423/210 |
| 4,889,654 | 12/1989 | Mason et al. | 252/100 |
| 5,006,326 | 4/1991 | Mayurnik et al. | 423/477 |
| 5,039,423 | 8/1991 | Kelley | 210/664 |
| 5,200,171 | 4/1993 | Ratcliff | 424/52 |
| 5,232,584 | 8/1993 | Wang et al. | 210/139 |
| 5,294,307 | 3/1994 | Jackson | 204/95 |
| 5,348,734 | 9/1994 | Ratcliff | 424/53 |
| 5,389,384 | 2/1995 | Jooste | 424/661 |
| 5,407,656 | 4/1995 | Roozdar | 423/477 |
| 5,447,551 | 9/1995 | Huestis et al. | 75/414 |
| 5,496,730 | 3/1996 | Teramachi | 435/290 |
| 5,547,584 | 8/1996 | Capehart | 210/669 |
| 5,738,840 | 4/1998 | Richter | 424/53 |

OTHER PUBLICATIONS

Sussman, S. et al., "Chlorine dioxide is an attractive treatment", Water Sewage Works, Ref. No. R–120–R–121 (1979)—Pollution Abs. 064720 80–01667.

Serper, "Odor Control Systems for Solid Waste Facilities: Review and Selection", Solid Wastes Management Refuse Removal Journal 21, 5, pp. 22–24, 28, 31 (1978)—see p. 1, lines 18–22.

Tollefsrud, "Hypochlorite Kills Lift Station Odor", Water Sewage Works 126, 1, p. 78 (1979)—see p. 1, lines 26–29.

Tomar et al., "Water, Air, Soil Pollution" 81 3–4, 385–399 (1995)—Chemical Abstracts 123:122054Z.

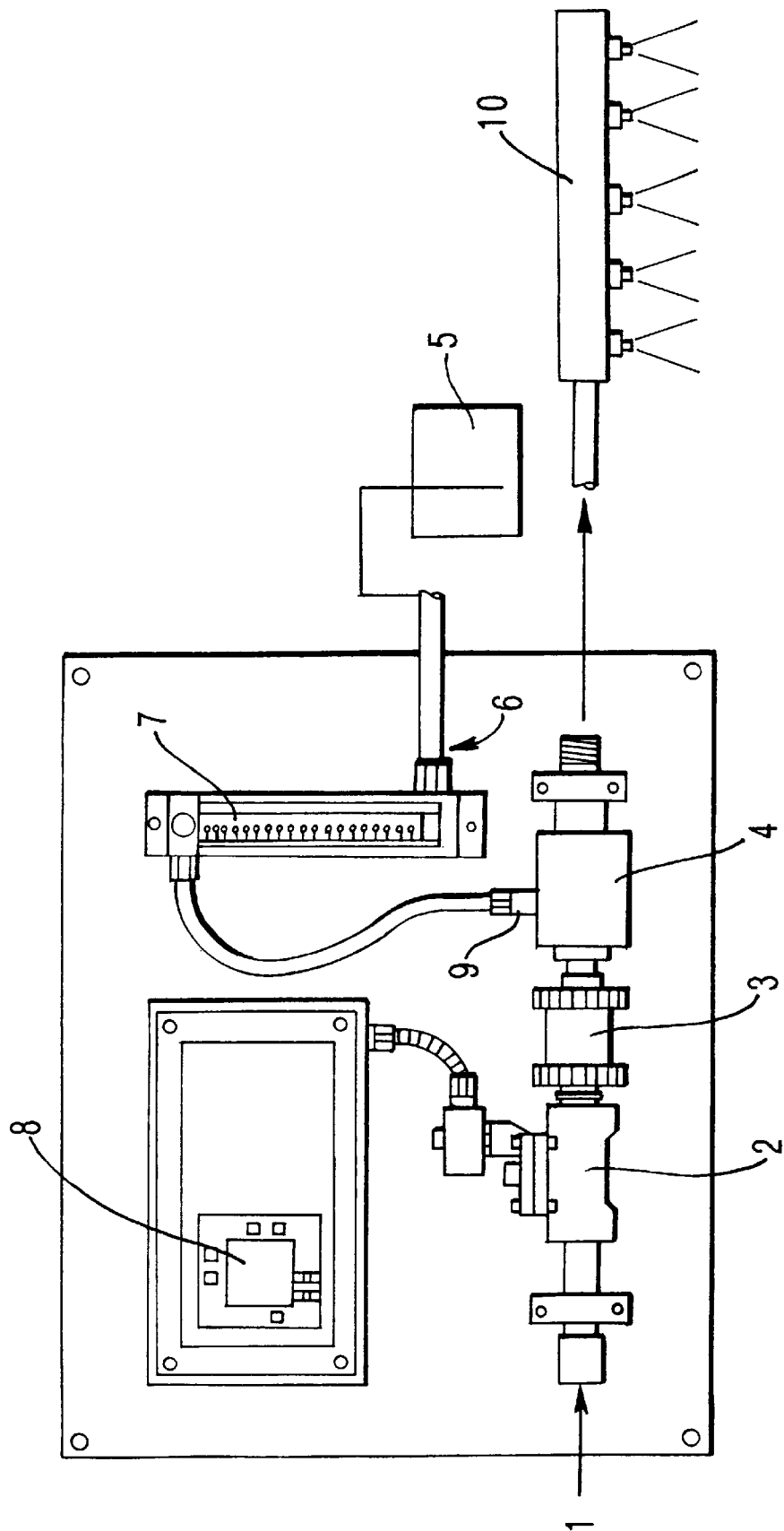

PROCESS AND APPARATUS FOR DEODORIZING MALODOROUS SUBSTANCES WITH A CHLORINE DIOXIDE-CONTAINING COMPOSITION

BACKGROUND OF THE INVENTION

This invention relates to a process and an apparatus for deodorizing malodorous substances.

Waste streams from sewage plants, rendering plants, barns and hog pens, as well as dung manure spreads and garbage-filled landfills, contain solids, liquids and/or gases from which foul odors may evolve. Such odors are objectionable to workers and inhabitants of the area, and in some cases, the odors are so objectionable as to cause partial or total shutdown of the facility.

Various schemes have been proposed for alleviating malodorous substances including aeration, incineration, scrubbing and/or deodorizing reactions.

Numerous methods involve the use of oxidizing agents. Waste or exhaust gas is deodorized by washing at least twice with active chlorine which is practically free from chlorine dioxide, followed by an alkaline washing (U.S. Pat. No. 3,923,955 issued Dec. 2, 1975 to Fattinger). Solid waste facilities are scrubbed for odor control with oxidizing agents such as sodium hypochlorite, chlorine, chlorine dioxide, or potassium permanganate (A. Serper, "Odor Control Systems for Solid Waste Facilities: Review and Selection", *Solid Wastes Management Refuse Removal Journal* 21, 5, pp. 22–24, 28, 31 (1978)—Pollution Abs. 054933-78-04121). Sewage farms and dung manure spreadings are sprayed with a composition comprising a stabilized aqueous solution of chlorine dioxide, isopropanol, didecyldimethyl ammonium chloride, a non-ionic surfactant, aromatic materials, stabilizing co-emulsifiers, and water (FR 2,696,643 A1 issued Apr. 15, 1994 to Rocchia—Derwent Abs. No. 94-146367/18). Waste gases from a sewage lift station are scrubbed with a hypochlorite solution produced electrolytically from a brine solution" (Tollefsrud, "Hypochlorite Kills Lift Station Odor", *Water Sewage Works* 126 1, p. 78 (1979)—C. A. 90 (16) 1127051f). Gases containing odiferous acidic contaminants are mist scrubbed with an aqueous reagent containing a mixture of an oxidizing agent and a base. Chlorine dioxide, hydrogen peroxide, ozone, sodium hypochlorite, or various permanganates may be used. Sodium hydroxide and sodium hypochlorite are commonly used (U.S. Pat. No. 4,844,874 issued Jul. 4, 1989). Hydrogen sulfide-laden process gas from the cooler-scrubber used in recycling spent reducing gas from a direct reduction iron oxide apparatus is contacted with a chlorine dioxide spray to oxidize the hydrogen sulfide to a water soluble sulfate (U.S. Pat. No. 5,447,551 issued Sep. 5, 1995 to Huestis et al.). Gases from fermentation compartments of an organic waste recycling apparatus are deodorized by serially connecting a circulatory pipe to a first deodorizing tank containing water, then to a second deodorizing tank containing a chlorine dioxide solution, preferably stabilized, and optionally to a third deodorizing tank containing activated carbon (U.S. Pat. No. 5,496,730 issued Mar. 5, 1996 to Teramachi).

The above deodorizing schemes have not been completely successful in eliminating foul odors and there is still a need for a more effective deodorizing composition, a process for its use, and an apparatus for its delivery.

SUMMARY OF THE INVENTION

The present invention provides a process for deodorizing malodorous substances selected from the group consisting of gases, liquids, and/or solids, by misting these substance(s) with an aqueous deodorizing solution consisting essentially of an alkali metal or alkaline earth metal chlorite, one or more buffering agents, water, and optionally an alkali metal or alkaline earth metal chlorate and/or an alkali metal or alkaline earth metal chloride. The deodorizing solution contains available chlorine dioxide and has a pH of about 8.5 to about 9.5. A concentrated deodorizing solution is usually provided and then diluted with sufficient water to provide the required amount of oxidizing agents, i.e., the available chlorine dioxide and the chlorite, which must be present in an amount sufficient to deodorize the malodorous substance(s). Alkali metal chlorite is preferred. The preferred alkali metal chlorite is sodium chlorite in which case the alkali metal chlorate is sodium chlorate, and the alkali metal chloride is sodium chloride. The amount of the available chlorine dioxide in a diluted deodorizing solution should be about 10 to about 1000 ppm, preferably about 50 to about 200 ppm. The amount of the sodium chlorite present in the concentrated deodorizing solution is about 67,000 to about 270,000 ppm, preferably about 135,000 to about 200,000 ppm. The particle size of the deodorizing mist should be sufficient to effect oxidation of the malodorous substance(s), preferably to oxidation products which have no odor or no foul odor. The buffering agents, e.g., a carbonate/bicarbonate mixture, are present in an amount sufficient to maintain the pH of the deodorizing solution at about 8.5 to about 9 prior to the misting. During the contact with the malodorous substances, the pH is reduced and the chlorine dioxide is made available.

The malodorous substance can be sewer gas present above sewage in the sewage tank(s) of a sewage lift station, the malodorous substance(s) above or near a solid waste dump, the malodorous substances above a pig or hog waste lagoon, the malodorous substances from a garbage dump, or substances from a land fill. The malodorous substances commonly associated with fecal matter include indoles and skatoles and sulfur-containing compounds including mercaptans and sulfides, particularly hydrogen sulfide.

An apparatus suitable for use in the above process comprises (a) a reservoir for supplying a concentrated deodorizing liquid; (b) a means for supplying water for diluting the aqueous deodorizing liquid; (c) an eductor for mixing the dilution water supplied and the deodorizing liquid supplied; (d) a means for controlling the amount of the aqueous deodorizing solution added to the eductor; (e) a plurality of spray nozzles for spraying the diluted mixed deodorizing liquid into the malodorous substances; (f) a means for carrying the supplied dilution water to the eductor; (g) a means for shutting off the supplied dilution water, which is connected to the supply water means; (h) a means for carrying the concentrated aqueous deodorizing solution from the reservoir to the eductor; and (i) a means for preventing back-flow and dilution of the concentrated deodorizing solution supplied from the reservoir to the eductor which is located after the rotameter and before the eductor and is connected to the means for carrying the concentrated deodorizing liquid. A suitable water supply means is a medium pressure water supply system. Preferably, the shut-off means is a solenoid valve and the back-flow prevention means is a ball check valve. A rotameter is used to control the amount of deodorizing solution added to the eductor and it is equipped with a polytetrafluoroethylene check valve. Preferably, the plurality of spray nozzles are serially connected. Preferably, a timer is connected to the solenoid shut-off valve.

DESCRIPTION OF THE PREFERRED EMBODIMENTS

The preferred concentrated deodorizing solution is Endimal®. Endimal® is a registered trademark of Pettibone Laboratories, North Kingston, R.I. Endimal® is a stabilized aqueous chlorine dioxide solution which contains about 50,000 to about 200,000 ppm of chlorine dioxide. It has a pH of about 8.5 to about 9.0. The Endimal® is diluted to an effective concentration and misted into or onto the malodorous substance using a spray nozzle and fluid velocity which gives the mist the required droplet size. The droplet size is particularly important, especially when gases are being deodorized. If the droplets are too large, intimate contact of the gas with the deodorizing mist is not possible and the droplets tend to rapidly move through the gas, precipitating before the oxidation is complete. If the droplets are too small, there is no intimate contact as the droplets tend to be carried off due to air flow, wind, etc.

As an example of the chemistry involved in the deodorization (i.e., oxidation) reaction, the removal of hydrogen sulfide from a sewage lift station is discussed below. When the hydrogen sulfide is contacted with water, such as that associated with the deodorizing composition, it tends to hydrolyze according to the following equation: $H_2S \rightarrow H^+ + HS^-$. The acidity of the resulting solution tends to release chlorine dioxide from the deodorizing solution. The released chlorine dioxide then reacts with the residual hydrogen sulfide according to the following equation: $2H_2S + 2ClO_2 \rightarrow H_2SO_4 + 2HCl + S$. The sulfuric acid and/or sulfur generated have no odor.

This same type of oxidation reaction can be used to deodorize other malodorous inorganic and organic compounds such as aldehydes, amines, mercaptans, acids, phenols, and the like. The oxidation of organic compounds generally results in the abatement of odor since the oxidation products, e.g., carbon dioxide and water, have little or no odor.

The apparatus used for carrying out the deodorizing process comprises a medium pressure water supply system (1) connected to a solenoid shut-off valve (2) through piping or tubing (3) which carries the water to an eductor (4). The eductor (4) creates a vacuum as the water flows through it. A reservoir (5) contains a concentrated deodorizing solution. A tube or pipe with a ball check valve (6) carries the concentrated deodorizing solution under the vacuum created in the eductor to the eductor (4) through a rotameter (7) which is equipped with a Teflon check valve (9) at its exit. The rotameter (7) measures the flow rates of the concentrated deodorizing solution to be added to the water from the water supply system (1) for dilution. The diluted deodorizing solution is then conducted under pressure from the eductor (4) to a series of spray nozzles (10) which are used for misting the substances to be deodorized. In a preferred embodiment, a timer (8) or monitor (8) is connected electrically to the solenoid shut-off valve (2) so that the apparatus may be operated intermittently or continuously. The monitor can be used to detect, for example, the hydrogen sulfide and determine if the deodorizing process should be continued or interrupted or if the amount of the deodorizing liquid being supplied should be increased or decreased. The water flow rate in the eductor (4) is determined by the orifice size of the eductor (4) and the pressure of the water flowing through the eductor (4). Curves are provided by each manufacturer for each different size eductor showing the flow rate of the water in gallons per minute as a function of water line pressure. Knowing the flow rate of the water through the eductor (4), one skilled in the art can determine the rotameter setting necessary to provide the desired parts per million (ppm) of chlorine dioxide to the substance(s) to be deodorized. The deodorizing solution is then conducted under pressure to a series of spray nozzles positioned to provide a spray pattern which covers the entire area to be treated.

In a specific example, the sewage gas odor was eliminated when a sewage lift station was equipped with the apparatus described above. Endimal® 1500 (a buffered aqueous solution of sodium chlorite containing 15% available chlorine dioxide) was educted through a rotameter set at 55 to a Capital Controls eductor (Nunber 6). This system delivered 1.8 gallons per day of Endimal® 1500 to the eductor which flows about 2.0 gallons per minute of water at 80 lbs/in$^2$ line pressure. The concentration of available chlorine dioxide in the diluted stream was about 112 ppm. The diluted deodorizing solution was then conducted to a series of about 20 spray nozzles arranged above the grating covering the sewage tank. The spray nozzles have a flow rate of 0.12 gallons per minute. They are SSTX-1 cone tip nozzles. The spray nozzles are arranged in a pattern which will provide complete coverage of the liquid surface with a mist having a droplet size of about 50 microns. Operation in this manner eliminated the malodor generated in the lift station. If the malodor reoccurred, the rotameter was turned up.

Now that the preferred embodiments of the invention have been described in detail, various modifications and improvements thereon will become readily apparent to those skilled in the art. Accordingly, the spirit and scope of the present invention are to be limited only by the appended claims and not by the specification.

What is claimed is:

1. A process for deodorizing malodorous gas(es) above or near sewers, solid waste dumps, garbage dumps, land fills, or waste lagoons, which comprises the step of misting the malodorous gas(es) with an aqueous deodorizing solution consisting essentially of an alkali metal chlorite, one or more buffering agents, and water, which solution contains available chlorine dioxide and has a pH of about 8.5 to about 9.5, with the available chlorine dioxide being about 10 to about 1000 ppm and with the available chlorine dioxide and alkali metal chlorite oxidizing agents being present in amounts sufficient to deodorize the malodorous gas(es) and with the particle size of the deodorizing mist being effective to oxidize the malodorous gas(es).

2. The process of claim 1, wherein the malodorous gases are the gases above or near the garbage dumps.

3. The process of claim 1, wherein the amount of the available chlorine dioxide is about 50 to about 220 ppm.

4. The process of claim 1, wherein the alkali metal chlorite is sodium chlorite present in an amount of about 13 to about 135 ppm.

5. The process of claim 3, wherein the alkali metal chlorite is sodium chlorite present in an amount of about 65 to about 280 ppm.

6. The process of claim 1, wherein the malodorous substances are selected from the group consisting of indoles, skatoles, sulfur-containing compounds, amine-compounds, and putricines.

7. The process of claim 6, wherein the sulfur-containing compound is hydrogen sulfide.

8. The process of claim 1, wherein the particle size of the deodorizing mist is about 5 to about 200 microns.

9. The process of claim 1, wherein the malodorous gases are the sewer gases above or near liquid sewage in sewage tanks of sewage lift stations.

10. The process of claim 1, wherein the malodorous gases are the gases above or near solid waste or dumps.

11. The process of claim 1, wherein the malodorous gases above or near the waste lagoons are from pig or hog waste lagoons.

12. The process of claim 1, wherein the malodorous gases are the gases above or near the land fills.

13. The process of claim 1, wherein the aqueous deodorizing solution further consists essentially of an alkali metal chlorate and/or an alkali metal chloride.

14. An apparatus for spraying malodorous substance(s) comprising:

a reservoir for supplying a concentrated aqueous deodorizing solution which consists essentially of an alkali metal chlorite, one or more buffering agents, and water, which solution contains available chlorine dioxide and has a pH of about 8.5 to about 9.5, with the alkali metal chlorite and the available chlorine dioxide oxidizing agents being present in an amount sufficient to deodorize the malodorous substance(s);

a means for supplying water for diluting the concentrated aqueous deodorizing solution;

an eductor for mixing the dilution water supplied and the concentrated aqueous deodorizing solution supplied;

a means for preventing back-flow and dilution of the concentrated aqueous deodorizing solution being added to the eductor;

a plurality of spray nozzles for spraying a deodorizing mist of the diluted and mixed deodorizing solution into or onto the malodorous substance(s), with the aqueous particle size of the deodorizing mist being sufficient to effect oxidation of the malodorous substance(s);

a means for carrying the supplied dilution water to the eductor;

a means for shutting off the supply of dilution water, which means is connected to the means for supplying the water for dilution;

a means for carrying the concentrated aqueous deodorizing solution from the reservoir to the eductor; and a means for shutting off the concentrated aqueous deodorizing solution supplied from the reservoir to the eductor, which means is located before the eductor and is connected to the means for carrying the concentrated aqueous deodorizing solution to the eductor.

15. The apparatus of claim 14, wherein the concentrated aqueous deodorizing solution contains about 67,000 to about 270,000 ppm of sodium chlorite as the alkali metal chlorite; wherein the diluted aqueous deodorizing solution contains about 10 to 1000 ppm of available chlorine dioxide; wherein the shut-off means is a solenoid valve; wherein the back-flow prevention means is a ball check valve; and wherein the means for controlling the amount of concentrated aqueous deodorizing solution added to the eductor is a rotameter which has an entrance attached to the reservoir and an exit attached to the eductor, which exit is equipped with a plastic tubing.

16. The apparatus of claim 15, wherein the concentrated aqueous deodorizing solution contains about 135,000 to about 200,000 ppm of sodium chlorite as the alkali metal chlorite; wherein the diluted aqueous deodorizing solution contains about 50 to 200 ppm of available chlorine dioxide; wherein the water supply means is a medium pressure water supply system; wherein the shut-off means is a solenoid valve; wherein the back-flow prevention means is a ball check valve; and wherein the means for controlling the amount of concentrated aqueous deodorizing solution added to the eductor is a rotameter which has an entrance attached to the reservoir and an exit attached to the eductor, which exit is equipped with a plastic tubing.

17. The apparatus of claim 15, wherein the plurality of spray nozzles are serially connected.

18. The apparatus of claim 15, further comprising a timer or a monitor connected to the solenoid shut-off valve.

19. The apparatus of claim 14 wherein the aqueous deodorizing solution further consists essentially of an alkali metal chlorate and/or an alkali metal chloride.

20. In an improved method of operating a sewage lift station which comprises a sewage tank having an inlet for sewage in the lower part thereof and a space for malodorous sewer gases above the sewage inlet, the improvement comprising the step of contacting malodorous sewer gases with an aqueous mist consisting essentially of sodium chlorite, one or more buffering agents, and water, which solution contains about 10 to 1000 ppm of available chlorine dioxide and has a pH of about 8.5 to about 9.5, with the sodium chlorite and the available chlorine dioxide oxidizing agents being present in an amount sufficient to deodorize the malodorous sewer gases and with the particle size of the deodorizing mist being effective to oxidize hydrogen sulfide gas and other malodorous substances in the sewer gases.

21. In the method of claim 20, wherein the sewage tank is covered with a grating; and wherein the aqueous deodorizing liquid is misted onto the sewer gases by transporting the aqueous deodorizing liquid through hoses having nozzles appropriately sized to the effective droplet size.

22. In the method of claim 21, wherein the hoses are placed on top of the grating; wherein the droplet size is about 50 microns; and wherein the amount of hydrogen sulfide remaining in the malodorous sewer gases is detected by a monitor and the misting is discontinued or continued based on the detected amount of hydrogen sulfide.

23. In the method of claim 20, wherein the aqueous deodorizing solution further consists essentially of an alkali metal chlorate and/or an alkali metal chloride.

* * * * *